United States Patent [19]

Janulis et al.

[11] Patent Number: 5,157,159
[45] Date of Patent: Oct. 20, 1992

[54] PROCESS FOR HYDROXYALKYLATION OF FLUORINATED ALCOHOLS

[75] Inventors: Eugene P. Janulis, Mahtomedi; Gary J. Drtina, Woodbury, both of Minn.

[73] Assignee: Minnesota Mining and Manufacturing Company, St. Paul, Minn.

[21] Appl. No.: 714,452

[22] Filed: Jun. 13, 1991

[51] Int. Cl.$^5$ .............................................. C07C 41/01
[52] U.S. Cl. ................................................... 568/677
[58] Field of Search ......................................... 568/677

[56] References Cited

U.S. PATENT DOCUMENTS

| | | | |
|---|---|---|---|
| 3,394,115 | 7/1968 | Sorkin | 260/89.5 |
| 3,470,258 | 9/1969 | Tesoru | 568/677 |
| 3,532,674 | 10/1970 | Banitt | 260/78.4 |
| 4,906,792 | 3/1990 | Heilmann | 568/812 |

FOREIGN PATENT DOCUMENTS 482433 4/1976 U.S.S.R. .

OTHER PUBLICATIONS

*Van Nostrand Chemists Dictionary*, Van Nostrand Company, Princeton, NJ 1953, p. 518.
T. Yoshino, et al., *Bull Chem. Soc. Japan*, 46, 553 (1973).
H. Niederpruem, et al., *Liebigs Ann. Chem.*, 11 (1973).

*Primary Examiner*—Marianne M. Cintins
*Assistant Examiner*—Rebecca Cook
*Attorney, Agent, or Firm*—Gary L. Griswold; Walter N. Kirn; Lorraine R. Sherman

[57] ABSTRACT

Mono O-hydroxyalkylated derivatives of 1,1-dihydroperfluorinated or 1H,1-alkylperfluorinated alcohols are prepared by reacting the alcohols with alkylene carbonates at a temperature of at least 60° C. in the presence of a one- or two-part catalyst. The catalyst is a nitrogenous base, optionally in combination with a tetraalkylammonium halide. The O-hydroxyalkylated derivatives are useful non-ionic surfactants and emulsifiable compounds for fire extinguishing systems.

12 Claims, No Drawings

PROCESS FOR HYDROXYALKYLATION OF FLUORINATED ALCOHOLS

FIELD OF THE INVENTION

This invention relates to a novel process for the preparation of O-hydroxyalkylated derivatives of 1,1-dihydroperfluorinated or 1H,1-alkylperfluorinated alcohols. The O-hydroxyalkylated derivatives are useful as intermediates in the preparation of liquid crystals, and as non-ionic surfactants and emulsifiable compounds for fire extinguishing systems.

BACKGROUND OF THE INVENTION

O-Hydroxyalkylation of 1,1-dihydroperfluorinated alcohols has most commonly been conducted using alkylene oxide reagents. U.S. Pat. No. 3,394,115, for example, teaches the O-hydroxyethylation of 2,2,2-trifluoroethanol using ethylene oxide. Despite employing a 1:1 stoichiometry of reactants, the monohydroxyethylated product was obtained in only 50 percent yield, with the simultaneous formation of the product resulting from addition of two molecules of ethylene oxide in 25 percent yield. The problem of polyalkylation was circumvented somewhat in U.S. Pat. No. 3,532,674 (Example 1, Method B). By slowly adding, over the course of several hours, two-thirds of an equivalent of ethylene oxide per equivalent of 1,1-dihydroperfluorinated alcohol, a reasonably good selectivity to the monohydroxyethylated product was achieved. The conversion (based on starting alcohol), however, was not indicated and, even so, the theoretical yield could only be 67 percent. The problem with alkylene oxides, aside from their toxicity and well-known explosion potential, is that they do not discriminate well between starting and product alcohols.

In contrast, alkylene carbonates have been utilized to provide O-hydroxyalkylated phenols (cf. T. Yoshino, et al., *Bull. Chem. Soc.* Japan, 46, 553 (1973)) and perfluoroalkanesulfonamides (cf. H. Niederpruem, et al., *Liebigs Ann. Chem*, 11 (1973)). Alkylene carbonates are stable, relatively inexpensive, non-toxic, and non-gaseous (at room temperature and pressure) compounds.

In related work, ethylene sulfite has been utilized to provide O-hydroxyethylated 1,1-dihydroperfluorinated alcohols (see U.S.S.R. 482,433 (1976)). Aside from the increased cost of the reagent, emission of the extremely acidic sulfur dioxide by-product can lead to significant processing and pollution problems.

A process for the O-hydroxyalkylation of 1,1-dihydroperfluorinated alcohols has been disclosed in U.S. Pat. No. 4,906,792. This process is particularly useful with alcohols with boiling points of at least 140° C.

SUMMARY OF THE INVENTION

The present invention provides an improved process for the mono O-hydroxyalkylation of 1,1-dihydroperfluorinated or 1H,1-alkylperfluorinated alcohols.

Briefly, the present invention involves reaction of 1,1-dihydroperfluoroalcohols or 1H,1-alkylperfluorinated alcohols with an alkylene carbonate in the presence of a catalyst. Alkylene carbonates react principally with 1,1-dihydroperfluorinated or 1H,1-alkylperfluorinated alcohols and not with the O-hydroxyalkylated alcohol products, thereby affording a high selectivity towards monoalkylation. Nitrogen-containing bases optionally in combination with tetraalkylammonium halides are effective and efficient catalysts in the hydroxyalkylation of 1,1-dihydroperfluoroalcohols or 1H,1-alkylperfluoroalcohols.

In particular, the present invention provides an improved process for the O-hydroxyalkylation of 1,1-dihydroperfluorinated or 1H,1-alkylperfluorinated alcohols with boiling points of less than 140° C.

The process of the present invention provides monoether products almost exclusively, in contrast to some of the other known methods which yield significant amounts of polyether by-products.

The O-hydroxyalkylated derivatives are useful as nonionic surfactants and emulsifiable compounds for fire extinguishing systems. Additionally, the O-hydroxyalkylated derivatives are useful synthetic intermediates to esters which are more hydrolytically stable, are less prone to crystallize, and are often more thermally stable than esters derived from the starting 1,1-dihydroperfluorinated or 1H,1-alkylperfluorinated alcohols.

In this application:
"alkyl" and "alkylene" mean the monovalent and divalent residues remaining after removal of one and two hydrogen atoms, respectively, from a linear or branched chain hydrocarbon having 1 to 20 carbon atoms;
"lower" alkyl means C-1 to C-4 alkyl;
"aryl" means the monovalent residue remaining after removal of a hydrogen atom from an aromatic compound (single ring and multi- and fused-cyclic) having 5 to 12 ring atoms and includes substituted aromatics such as lower alkaryl and aralkyl, lower alkoxy, N,N-di(lower alkyl)amino, nitro, cyano, halo, and lower alkyl carboxylic acid ester, wherein "lower" means C-1 to C-4;
"cycloalkyl" means the monovalent residue remaining after removal of a hydrogen atom from a saturated cyclic hydrocarbon having 3 to 12 carbon atoms;
"essentially pure" means greater than 90 weight percent of the desired compound; and
"substantially perfluorinated" means hydrocarbon groups in which at least 50 percent of the hydrogen atoms have been replaced by fluorine.

DESCRIPTION OF PREFERRED EMBODIMENTS OF THE INVENTION

This invention provides a method for the preparation of essentially pure mono O-hydroxyalkylated 1,1-dihydroperfluorinated or 1H,1-alkylperfluorinated alcohols, the method being accomplished by reaction of a 1,1-dihydroperfluorinated or 1H,1-alkylperfluorinated alcohol of Formula I:

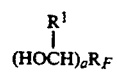

wherein
$R^1$ is hydrogen or lower alkyl;
a is 1 or 2; and
$R_F$ is a alkyl, cycloalkyl, or aryl group when a is 1, and fluorinated alkylene when a is 2, with an alkylene carbonate of Formula II:

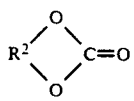

wherein

R² is an alkylene group having 2 to 4 carbon atoms, in the presence of an effective amount of a catalyst to produce an O-hydroxyalkylated compound having Formula III:

wherein $R^1$, $R^2$, a, and $R_F$ are as defined above.

Many of the fluorinated alcohols of Formula I useful in the invention are commercially available. These include
2,2,2-trifluoroethanol;
2,2,3,3-tetrafluoro-1,4-butanediol;
1H,1H,3H-tetrafluoro-1-propanol;
3,3,4,4-pentafluoro-2-butanol;
1H,1H-pentafluoro-1-propanol;
2,2,3,3,4,4-hexafluoro-1,5-pentanediol;
1H,1H-heptafluoro-1-butanol;
1,1,1,2,2,3,3-heptafluoro-4-octanol;
3,3,4,4,5,5,5-heptafluoro-2-pentanol;
3,3,4,4,5,5,6,6-octafluoro-2-heptanol;
1H,1H,6H,6H-octafluorohexanediol;
1H,1H,5H-octafluoro-1-pentanol;
2,2,3,3,4,4,5,5,6,6-decafluoro-1-methylheptan-1-ol;
undecafluorocyclohexylmethanol;
1H,1H,7H-dodecafluoro-1-heptanol;
1H,1H-pentadecafluorooctan-1-ol;
1H,1H,9H-hexadecafluoro-1-nonanol; and
1H,1H,11H-eicosafluoro-1-undecanol.

Suitable alkylene carbonates of formula II include ethylene carbonate, propylene carbonate, and 1,3-dioxan-2-one, with ethylene carbonate being preferred. The alkylene carbonates are available from Aldrich Chemical Co.

The catalyst used in the process of the present invention can be a single catalyst designated A, or a combination of two catalysts, A+B.

"A" catalysts can be nitrogenous bases such as aliphatic or aromatic tertiary amines. Preferably the nitrogenous bases are trisubstituted alkylamines, wherein the alkyl groups are independently selected from alkyl groups having 1 to 20 carbon atoms. Representative nitrogenous bases useful in the present invention include triethylamine, tributylamine, trihexylamine, and imidazole, all of which are commercially available from Aldrich Chemical Co.

"B" catalysts can be any of the tetraalkylammonium halides wherein halide can be chloride, bromide, or iodide, and the alkyl group can be independently selected from alkyl groups having 1 to 20 carbon atoms. Representative examples include tetrabutyl ammonium iodide, tetramethylammonium iodide, and tetraethylammonium bromide. Preferred anions are bromide or iodide. These catalysts are commercially available from Aldrich Chemical Co.

The reaction is most efficiently conducted by mixing an 1,1-dihydroperfluorinated or 1H,1-alkylperfluorinated alcohol; 1.00–3.00 equivalents (based on the alcohol), preferably 1.25–1.75 equivalents, of an alkylene carbonate; 0.01–5 equivalents (based on the alcohol), preferably 0.75–1.25 equivalents, of a nitrogenous base; and optionally 1.00–10.00 weight percent (based on alcohol) of a tetraalkylammonium halide catalyst, preferably 2.00–5.00 weight percent of the tetraalkylammonium halide catalyst. The reaction mixture is then warmed to at least 60° C., preferably in the range of 90°–140° C., until gas emission, i.e. carbon dioxide, ceases. The reaction mixture is then cooled. The nitrogeneous base can then be removed by distillation if its boiling point is lower than that of the resulting product. The resulting O-hydroxyalkylated product is obtained by distillation.

If the O-hydroxyalkylated products are further alkylated at all in the process, it probably derives from alkylene oxide formation from the alkylene carbonate. This takes place slowly at the above specified reaction temperatures but occurs at appreciable rates at temperatures above 160° C. (for the preferred ethylene carbonate).

The mono O-hydroxyalkylated 1,1-dihydroperfluorinated or 1H,1-alkylperfluorinated alcohol products of the invention possess both hydrophobic ($R_F$) and hydrophilic (O—$R^2$—OH) regions and are potent surface active agents. Therefore, the alcohol products find utility as non-ionic surfactants in a variety of applications including fire extinguishing systems because of their ability to float water on top of gasoline and organic liquids. Furthermore, the O-hydroxyalkylated products are useful reactants for synthesizing carboxylic acid esters. Because the less acidic O-hydroxyalkylated alcohol products make poorer leaving groups in hydrolysis reactions, these ester products are more hydrolytically stable then those derived from 1,1-dihydroperfluorinated alcohols. Another benefit is that incorporation of an ether group provides a "swivel" action to the ester group which inhibits crystallization. This is especially useful in acrylate or acrylamidoacylated ester monomer products and their utilization in UV curing situations which are most preferably performed in the absence of solvents. In addition, the products of the invention are useful intermediates in the preparation of low viscosity liquid crystals.

Objects and advantages of this invention are further illustrated by the following examples, but the particular materials and amounts thereof recited in these examples, as well as other conditions and details, should not be construed to unduly limit this invention. In all Examples the identity of the product was confirmed by spectral analysis (IR, $^1$H-NMR, and $^{13}$C-NMR spectroscopy) and purity was determined by gas chromatography.

EXAMPLE 1

2,2,2-Trifluoroethanol (10.0 g, 0.10 mol), triethylamine (10.1g, 0.10 mol), ethylene carbonate (13.2 g, 0.15 mol) and tetrabutyl ammonium iodide (0.74 g) were heated in a flask fitted with a reflux condenser under nitrogen in an oil bath at 100° C. for 1 day. The triethylamine and unreacted alcohol were removed by distillation. The product 2-(2,2,2-trifluoroethoxy)ethanol, b.p. 138° C., was obtained in 61% yield (8.6 g) of 97% pure material.

EXAMPLES 2-11

EXAMPLES 2-11 utilized the same components and procedure as EXAMPLE 1 except for the amine base used. The amine base used, amount of amine base when present, yield of product, i.e., 2-(2,2,2-trifluoroethoxy)e- thanol obtained, and purity of product, are shown in TABLE 1 below.

TABLE I

| Example | Amine Base "A" | Amount of amine base (mol) | Tetrabutyl ammonium iodide (g) "B" | Yield of Product* % |
|---|---|---|---|---|
| 2 | triethylamine | 0.05 | 0.74 | 54 |
| 3 | tributylamine | 0.10 | 0.74 | 74 |
| 4 | trihexylamine | 0.10 | 0.74 | 56 |
| 5 | imidazole | 0.10 | 0.74 | 42 |
| 6 | tributylamine | 0.01 | 0.74 | 42 |
| 7 | trihexylamine | 0.01 | 0.74 | 27 |
| 8 | triethylamine | 0.10 | 0.74 | 72 |
| 9 | tributylamine | 0.10 | 0 | 66 |
| 10 | trihexylamine | 0.10 | 0 | 60 |
| 11 | triethylamine | 0.10 | 0 | 61 |

*2-(2,2,2-trifluoroalkoxy)ethanol

EXAMPLE 12

1,1-dihydroperfluorobutanol (20.0 g, 0.10 mol), triethylamine (10.1g, 0.10 mol), ethylene carbonate (13.2 g, 0.15 mol) and tetrabutyl ammonium iodide (0.74 g) were heated in a flask fitted with a reflux condenser under nitrogen in an oil bath at 100° C. for 1 day. The triethylamine and unreacted alcohol were distilled off before the product 2-(2,2,3,3,4,4,4-heptafluorobutoxy)ethanol, b.p. 80° C. (30 mm), was obtained in 70% yield of 97% pure material.

The product was useful in the preparation of low viscosity liquid crystals.

EXAMPLE 13

The components and procedure used were the same as in EXAMPLE 12 except no tetrabutylammonium iodide ("B" catalyst) was used and the reaction time was 16 hours. Isolation was as in EXAMPLE 12 to afford the product 2-(2,2,3,3,4,4,4-heptafluorobutoxy)ethanol in 62% yield.

EXAMPLE 14

1,1,3-trihydroperfluoropropanol (1 equivalent), triethylamine (1 equivalent) and ethylene carbonate (1.5 equivalents) were heated in a flask fitted with a reflux condenser under nitrogen in an oil bath at 95° C. for 16 hours. The triethylamine and unreacted alcohol were distilled off and the product 2-(2,2,3,3-tetrafluoropropoxy)ethanol in 67% yield after vacuum distillation.

EXAMPLE 15

1,1-dihydroperfluoropropanol (1 equivalent), triethylamine (1 equivalent) and ethylene carbonate (1.5 equivalents) were heated in a flask fitted with a reflux condenser under nitrogen in an oil bath at 95° C. for 16 hours. The triethylamine and unreacted alcohol were distilled off and the product 2-(2,2,3,3,3-pentafluoropropoxy)ethanol in 72% yield after vacuum distillation.

EXAMPLE 16

1,1,5-trihydroperfluoropentanol (1 equivalent), triethylamine (1 equivalent) and ethylene carbonate (1.5 equivalents) were heated in a flask fitted with a reflux condenser under nitrogen in an oil bath at 95° C. for 16 hours. The triethylamine was removed by aqueous acid extraction and unreacted alcohol was distilled off and the product 2-(2,2,3,3,4,4,5,5-octafluoropentyloxy)ethanol in 65% yield after vacuum distillation.

EXAMPLE 17

1,1-dihydroperfluorooctanol (1 equivalent), triethylamine (1 equivalent) and ethylene carbonate 91.5 equivalents) were heated in a flask fitted with a reflux condenser under nitrogen in an oil bath at 95° C. for 28 hours. The triethylamine was removed by aqueous acid extraction and unreacted alcohol was distilled off and the product 2-(2,2,3,3,4,4,5,5,6,6,7,7,8,8,8-pentadecafluorooctyloxy)ethanol in 66% yield after vacuum distillation.

Various modifications and alterations of this invention will become apparent to those skilled in the art without departing from the scope and spirit of this invention, and it should be understood that this invention is not to be unduly limited to the illustrative embodiments set forth herein.

We claim:

1. A process comprising the steps:
    a) reacting
        (1) a fluorinated alcohol having the formula

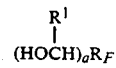

wherein
        $R^1$ is hydrogen or lower alkyl;
        a is 1 or 2; and
        $R_F$ is a fluorinated alkyl, cycloalkyl, or aryl group wherein at least 50 percent of the hydrogen atoms have been replaced by fluorine when a is 1, and fluorinated alkylene wherein at least 50 percent of the hydrogen atoms have been replaced by fluorine when a is 2; with
        (2) an alkylene carbonate having the formula

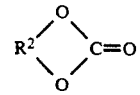

wherein
        $R^2$ is an alkylene group having 2 to 4 carbon atoms;
        (3) in the presence of an effective amount of a catalyst consisting of a nitrogenous base selected from the group consisting of aliphatic and aromatic tertiary amines; and
    b) isolating the resulting O-hydroxyalkylated derivative of said fluorinated alcohol having the formula

wherein $R^1$, $R^2$, a, and $R_F$ are as defined above.

2. The process according to claim 1 wherein said fluorinated alcohols are selected from the group consisting of
2,2,2-trifluoroethanol;
2,2,3,3-tetrafluoro-1,4-butanediol;
1H,1H,3H-tetrafluoro-1-propanol;
3,3,4,4,4-pentafluoro-2-butanol;
1H1H-pentafluoro-1-propanol;
2,2,3,3,4,4-hexafluoro-1,5-pentanediol;
1H,1H-heptafluoro-1-butanol;

1,1,1,2,2,3,3-heptafluoro-4-octanol;
3,3,4,4,5,5,5-heptafluoro-2-pentanol;
3,3,4,4,5,5,6,6-octafluoro-2-heptanol;
1H,1H,6H,6H-octafluorohexanediol;
1H,1H,5H-octafluoro-1-pentanol;
2,2,3,3,4,4,5,5,6,6-decafluoro-1-methylheptan-1-ol;
undecafluorocyclohexylmethanol;
1H,1H,7H-dodecafluoro-1-heptanol;
1H,1H-pentadecafluorooctan-1-ol;
1H,1H,9H-hexadecafluoro-1-nonanol; and
1H,1H,11H,-eicosafluoro-1-undecanol.

3. The process according to claim 1 wherein said alcohol is 1,1-dihydroperfluoro-1-octanol.

4. The process according to claim 1 wherein said alkylene carbonate is ethylene carbonate.

5. The process according to claim 1 wherein said catalyst is a trisubstituted alkylamine.

6. The process according to claim 1 wherein said A catalyst is selected from the group consisting of triethylamine, tributylamine, trihexylamine, and imidazole.

7. The process according to claim 1 wherein said alkylene carbonate is present in the range of 1.00 to 3.00 equivalents based on the alcohol.

8. The process according to claim 1 wherein said alkylene carbonate is present in the range of 1.25 to 1.75 equivalents based on the alcohol.

9. The process according to claim 1 wherein said catalyst is present in the range of 0.01 to 5.0 equivalents based on the alcohol.

10. The process according to claim 1 wherein said catalyst is present in the range of 0.75 to 1.25 equivalents based on the alcohol.

11. The process according to claim 1 wherein said reaction mixture is heated at a temperature of at least 60° C.

12. The process according to claim 1 wherein said reaction mixture is heated at a temperature in the range of 90° to 140° C.

* * * * *

UNITED STATES PATENT AND TRADEMARK OFFICE
CERTIFICATE OF CORRECTION

PATENT NO. : 5,157,159
DATED     : October 20, 1992
INVENTOR(S) : Eugene P. Janulis It is certified that error appears in the above-identified patent and that said Letters Patent is hereby corrected as shown below:

Col. 2, line 66, "$R_F$ is a" should be followed by -- fluorinated --.

Co. 6, line 66, "1H1H-pentafluoro-1-propanol" should be -- 1H,1H-pentafluoro-1-propanol --.

Col. 8, line 1, "said A" should read only -- said --.

Signed and Sealed this

First Day of February, 1994

Attest:

BRUCE LEHMAN

*Attesting Officer*    Commissioner of Patents and Trademarks